US011555056B2

(12) United States Patent
Kim et al.

(10) Patent No.: US 11,555,056 B2
(45) Date of Patent: Jan. 17, 2023

(54) METHODS AND MATERIALS FOR TREATING CANCER

(71) Applicants: Mayo Foundation for Medical Education and Research, Rochester, MN (US); Board of Regents, The University of Texas System, Austin, TX (US)

(72) Inventors: Yon Son Betty Kim, Jacksonville Beach, FL (US); Wen Jiang, Houston, TX (US); Christina Von Roemeling, Jacksonville, FL (US)

(73) Assignees: Mayo Foundation for Medical Education and Research and Board of Regents, Rochester, MN (US); The University of Texas System, Austin, TX (US)

( * ) Notice: Subject to any disclaimer, the term of this patent is extended or adjusted under 35 U.S.C. 154(b) by 93 days.

(21) Appl. No.: 16/607,939

(22) PCT Filed: Apr. 26, 2018

(86) PCT No.: PCT/US2018/029505
§ 371 (c)(1),
(2) Date: Oct. 24, 2019

(87) PCT Pub. No.: WO2018/200766
PCT Pub. Date: Nov. 1, 2018

(65) Prior Publication Data
US 2021/0094987 A1    Apr. 1, 2021

Related U.S. Application Data

(60) Provisional application No. 62/490,370, filed on Apr. 26, 2017.

(51) Int. Cl.
*C07K 14/36* (2006.01)
*C07K 16/28* (2006.01)
*C07K 16/30* (2006.01)
*C07K 16/32* (2006.01)

(52) U.S. Cl.
CPC .......... *C07K 14/36* (2013.01); *C07K 16/2863* (2013.01); *C07K 16/3069* (2013.01); *C07K 16/32* (2013.01); *C07K 2319/33* (2013.01)

(58) Field of Classification Search
CPC ................ C07K 14/36; C07K 16/2863; C07K 16/3069; C07K 16/32; C07K 2319/33
See application file for complete search history.

(56) References Cited

U.S. PATENT DOCUMENTS

| | | | |
|---|---|---|---|
| 6,365,161 B1 | 4/2002 | Deo et al. | |
| 6,518,397 B1 | 2/2003 | Dedhar | |
| 7,488,711 B2 | 2/2009 | Tosato et al. | |
| 9,095,568 B2 | 8/2015 | Berninger et al. | |
| 9,527,906 B2 | 12/2016 | Gelfand et al. | |
| 10,556,965 B2 | 2/2020 | Kim et al. | |
| 11,034,773 B2 | 6/2021 | Kim et al. | |
| 2003/0113332 A1 | 6/2003 | Mathew et al. | |
| 2005/0008649 A1 | 1/2005 | Shin et al. | |
| 2006/0093612 A1 | 5/2006 | Srivastava | |
| 2013/0078249 A1 | 3/2013 | Ast et al. | |
| 2013/0121918 A1 | 5/2013 | Hong et al. | |
| 2013/0121958 A1 | 5/2013 | Leclerc et al. | |
| 2014/0242079 A1 | 8/2014 | Bacac et al. | |
| 2014/0271683 A1 | 9/2014 | Chao et al. | |
| 2014/0271687 A1 | 9/2014 | Kovesdi et al. | |
| 2017/0218086 A1 | 8/2017 | Kim et al. | |
| 2020/0216561 A1 | 7/2020 | Kim et al. | |
| 2021/0179673 A1 | 6/2021 | Kim et al. | |

FOREIGN PATENT DOCUMENTS

| | | |
|---|---|---|
| CN | 103735514 | 4/2014 |
| EP | 3138581 | 3/2012 |
| WO | WO 1996/016673 | 6/1996 |
| WO | WO 2008/032153 | 3/2008 |
| WO | WO 2010/051635 | 5/2010 |
| WO | WO 2012/088309 | 6/2012 |
| WO | WO 2015/138600 | 9/2015 |

OTHER PUBLICATIONS

Basu et al., "CD91 is a common receptor for heat shock proteins gp96, hsp90, hsp70, and calreticulin," Immunity., Mar. 2001, 14(3):303-313.
Brunekreeft et al., "Targeted delivery of CD40L promotes restricted activation of antigen-presenting cells and induction of cancer cell death," Molecular cancer, Dec. 2014, 13(1):85.
Chao et al., "Calreticulin is the dominant pro-phagocytic signal on multiple human cancers and is counterbalanced by CD47," Sci .Transl. Med., Dec. 2010, 2(63):63ra94.
Emanuel, "The solution to drug prices," New York Times, Sep. 2015, 2 pages.
Extended European Search Report in European Application No. 18790016.2 dated Apr. 9, 2020, 12 pages.
Gan et al., "The Epidermal Growth Factor Receptor Variant III (EGFRvIII): Where Wild Things Are Altered," Febs J., Nov. 2013, 280(21):5350-70.
Giodini et al., "Receptor-mediated phagocytosis elicits cross-presentation in nonprofessional antigen-presenting cells," Proceedings of the National Academy of Sciences, Mar. 2009, 106(9):3324-9.
Houot et al., "T-cell-based Immunotherapy: Adoptive Cell Transfer and Checkpoint Inhibition," Cancer Immunol, Res., Oct. 2015, 3(10):1115-1122.
International Preliminary Report on Patentability in International Application No. PCT/US2018/029505 dated Oct. 29, 2019, 7 pages.

(Continued)

*Primary Examiner* — Ruixiang Li
(74) *Attorney, Agent, or Firm* — Fish & Richardson P.C.

(57) ABSTRACT

This document provides methods and materials involved in treating cancer. For example, methods and materials for using a BiPE that can include (a) one or more molecules having the ability to bind to a cancer cell (e.g., a human breast cancer cell), (b) an optional linker component, and (c) one or more molecules having the ability to bind to an antigen presenting cell (e.g., a human macrophage) to treat cancer are provided.

9 Claims, 4 Drawing Sheets

(56) References Cited

OTHER PUBLICATIONS

International Search Report & Written Opinion in International Application No. PCT/US2018/029505 dated Jul. 17, 2018, 33 pages.
Liu et al., "Rapid water disinfection using vertically aligned MoS 2 nanofilms and visible light," Nature nanotechnology, Dec. 2016, 11(12):1098.
Mellman I, Coukos G, Dranoff G. Cancer immunotherapy comes of age. Nature. Dec. 2011;480(7378):480-9.
Mitri et al., "The HER2 Receptor in Breast Cancer: Pathophysiology, Clinical Use, and New Advances in Therapy," Chemother, Res. Pract., 2012, 2012:743193.
Stewart and Wild, World Cancer Report 2014, IARC Publications, 2014, 632 pages.
Wang et al., "Current advances in T-cell-based cancer immunotherapy," Immunotherapy, Dec. 2014, 6(12): 1265-78.
Cavallo, Blocking CD47 Signals May Offer New Therapeutic Approach in the Treatment of Pancreatic Cancer, 2014, ascopost, http://www.ascopost.com/News/16233, pp. 1-4. (Year: 2014).
Chen et al., "SLAMF7 is critical for phagocytosis of haematopoietic tumour cells via Mac-1 integrin," Nature, 544(7651):493-497, Apr. 2017.
Dominguez and Lustgarten, "Targeting the tumor microenvironment with anti-neu/anti-CD40 conjugated nanoparticles for the induction of antitumor immune responses," Vaccine., 28(5): 1383-1390, Feb. 3, 2010.
Dong et al., "Induction of protective immunity against mycobacterium tuberculosis by delivery of ESX antigens into airway dendritic cells," Mucosal Immunology, May 2013, 6(3):522-534.
Fadeel et al, "Buried alive: a novel approach to cancer treatment," Faseb J., 18(1):1-4, Jan. 2004.
GenBank Accession No. Q8BHK6.2, "RecName: Full=SLAM family member 7: AltName: Full=Leukocyte cell-surface antigen; AltName: Full=Novel Ly9; AltName: CD_antigen=CD319; Flags: Precursor," dated Jan. 7, 2015, 4 pages.
GenBank Accession No. Q9NQ25.1, "RecName: Full=SLAM family member 7; AltName: Full=CD2 subset 1; AltName: Full=CD2-like receptor-activating cytotoxic cells; Short=CRACC; AltName: Full=Membrane protein FOAP-12; AltName: Full=Novel Ly9; AltName: Full=Protein 19A; AltName: CD_antigen=CD319; Flags: Precursor," dated Jan. 7, 2015, 7 pages.
Gogishvili et al., "SLAMF7-CAR T cells eliminate myeloma and confer selective fratricide of SLAMF7+ normal lymphocytes," Blood, 130(26):2838-2847, Dec. 2017.
Jenkins el aL "Mechanisms of resistance to immune checkpoint inhibitors," Br. J. Cancer, 118(1 ):9-16, Jan. 2018.
Jiang et al., "Design and characterization of lysine cross-linked mercapto-acid biocompatible quantum dots," Chem Mater., 18(4):872-878, 2006.
Kang et al., "Enhancing Glioblastoma-Specific Penetration by Functionalization of Nanoparticles with an Iron-Mimic Peptide Targeting Transferrin/Transferrin Receptor Complex," Mol Pharmaceutics., 12(8):2947-2961, 2015.
Klarquist and Janssen, "Melanoma-infiltrating dendritic cells. Limitations and opportunities of mouse models," Oncoimmunology., 1(9): 1584-1593, Dec. 1, 2012.
Kumaresan et al., "CS1, a novel member of the CD2 family, is homophilic and regulates NK cell function," Molecular immunology, 39(1-2):1-8, Sep. 2002.
Lehmann et al., "Direct Delivery of Antigens to Dendritic Cells via Antibodies Specific for Endocytic Receptors as a Promising Strategy for Future Therapies," Vaccines, Jun. 2016, 4(2):8, 32 pages.
Malaer and Mathew "CS1 (SLAMF7, CD319) is an effective immunotherapeutic target for multiple myeloma," American journal of cancer research, 7(8):1637, Aug. 2017.
Mosser and Zhang., "Activation of Murine Macrophages," Curr Protoc Immunol., 83:14.2.1-14.2.8, Nov. 1, 2008.
Obeid et al., "Calreticulin exposure dictates the immunogenicity of cancer cell death," Nat Med., 13(I):54-61, Jan. 2007.

Pazina et al., "The anti-SLAMF7 antibody elotuzumab mediates NK cell activation through both CD16-dependent and -independent mechanisms," Oncoimmunology, Jun. 2017, 6(9):e1339853.
Qie et al., "Surface modification of nanoparticles enables selective evasion of phagocytic clearance by distinct macrophage phenotypes," Sci Rep., 6:26269, May 19, 2016.
Shao et al. Nanoparticle-Based Immunotherapy for Cancer, 2015, ACSNANO, vol. 9, No. 1, pp. 16-30. (Year: 2015).
Stephan and Irvine, "Enhancing cell therapies from the outside in: Cell surface engineering using synthetic nanomaterials," Nanotoday., 6(3):309-325, Jun. 1, 2011.
Velmurugan et ah, "Phagocytosis of antibody-opsonized tumor cells leads to the formation of a discrete vacuolar compartment in macrophages," Traffic, Apr. 2018, 19(4):273-284.
Weiskopf et al., "Engineered SIRPa Variants as Immunotherapeutic Adjuvants to Anticancer Antibodies," Science., 341(6141):88-91, Jul. 5, 2013.
Wu et al., "Whole-cell vaccine coated with recombinant calreticulin enhances activation of dendritic cells and induces tumour-specific immune responses," Oncology Reports., 29(2):529-534, Feb. 2013.
Yuan et al., "Multivalent Bi-Specific Nano-Bioconjugate Engager for Targeted Cancer Immunotherapy," Nat Nanotechnol., 12(8):763-769, Aug. 2017.
Zhang et al., "Combating HER2-overexpressing breast cancer through induction of calrecticulin exposure by Tras-Permut CrossMab," Oncoimmunology., 4(3):e994391, Mar. 2015, 13 pages.
U.S. Appl. No. 15/417,721, filed Jan. 27, 2017, Yon Son Betty Kim, Issued as U.S. Pat. No. 10,556,965.
U.S. Appl. No. 16/726,571, filed Dec. 24, 2019, Yon Son Betty Kim, Issued as U.S. Pat. No. 11,034,773.
U.S. Appl. No. 17/263,689, filed Jan. 27, 2021, Yon Son Betty Kim, Published as U.S. Patent Application Publication No. 2021/0179673.
[No Author], "Calreticulin Serves as an "Eat Me" Signal," Science's STKE, Oct. 25, 2005, 307:tw375, 3 pages.
Benz, Edward J.; The Jeremiah Metzinger lecture cancer in the twenty first century: an inside view from an outsider. Trans. Am. Clin. Climatological Ass. (2017) 128 p. 275-297.
Gardai et al., "Cell-surface calreticulin initiates clearance of viable or apoptotic cells through trans-activation of LRP on the phagocyte" Cell, Oct. 21, 2005, 123(2):321-334.
Guo, Haiwei et al.; "Protein tolerance to random amino acid change." PNAS (2004) 101(25) p. 9205-9210.
Jokiranta, T. Sakari and Meri, Seppo; "Biotinylation of monoclonal antibodies prevents their ability to activate the classical pathway of complement." J. Immunol. (1993) 151(4) p. 2124-2131.
Muguruma, Kyohei et al.; "Novel hybrid compound of a plinabulin prodrug with an igg binding peptide for generating a tumor selective noncovalent type antibody drug conjugate." Bioconjugate Chem. (2016) 27 p. 1606-1613.
Peltomaa, Riika et al.; "Phage display in the quest for new selective recognition elements for biosensors." ACS Omega (2019) 4 p. 11569-11580.
Reynolds, Fred et al.; "A functional proteomic method for biomarker discovery." PLoS ONE (2011) 6(7) e22471).
Saldana, Jose Ignacio; "Macrophages" https://www.immunology.org/public-information/bitesized-immunology/cells/macrophages, downloaded Mar. 30, 2022.
Sano, Takeshi and Cantor, Charles R.; "A streptavidin protein a chimera that allows one step production of a variety of specific antibody conjugates." Biotechnology (1991)9 p. 1378-1381.
Sigma Aldrich catalog page for compound B4501 (biotin), downloaded Mar. 30, 2022.
Stamova, Slava et al.; "Cancer immunotherapy by retargeting of immune effector cells via recombinant bispecific antibody constructs." Antibodies (2012) 1 p. 172-198.
Yampolsky, Lev Y. and Stoltzfus, Arlin; The exchangeability of amino acids in proteins. Genetics (2005) 170 p. 1459-1472.
Singh, Bhagirath et al, "Minimum peptide sequences necessary for priming and triggering of humoral and cell mediated immune responses in mice: use of synthetic peptide antigens of defined structure." J. Immunol. (1980) 124(3) p. 1336-1343.

| hGBM Cell Line | Baseline GFP Expression (%) | Pre-sort EGFRvIII-GFP Expression (%) | Post-sort EGFRvIII-GFP Expression (%) |
|---|---|---|---|
| LN229 | 0 | 15.2 | 34 |
| U118 | 0 | 8.3 | 85.2 |
| U251 | 0 | 14.2 | 78.9 |

METHODS AND MATERIALS FOR TREATING CANCER

CROSS-REFERENCE TO RELATED APPLICATIONS

This application is a National Stage application under 35 U.S.C. § 371 of International Application No. PCT/US2018/029505, having an International Filing Date of Apr. 26, 2018, which claims priority to U.S. Application Ser. No. 62/490,370, filed on Apr. 26, 2017. The disclosures of the prior applications are considered part of the disclosure of this application, and are incorporated in their entirety into this application.

BACKGROUND

1. Technical Field

This document relates to methods and materials involved in treating cancer. For example, this document relates to methods and materials involved in using bi-specific phagocyte engagers (BiPEs) to treat cancer.

2. Background Information

The innate immune system is integral to the host's defense against foreign pathogens and essential to mediate cellular homeostasis. The first lines of defense are the professional antigen presenting cells (APCs) of the innate immune system, the gatekeepers of the body's immune system. These cells are designed to detect and eradicate infected or diseased cells (via phagocytosis) within the body and process cellular components and proteins and present them as antigens to the adaptive immune system. The innate immune system alone, however, does not confer patient-specific or disease-specific clearance, nor does it have the ability to generate long-lasting immune memory. The memory and immune surveillance programs for the host are mediated by a more specialized and highly specific adaptive immune system involving T-cells.

SUMMARY

This document provides methods and materials involved in treating cancer. For example, this document provides methods and materials for using BiPEs to treat cancer. A BiPE described herein can include (a) one or more molecules having the ability to bind to a cancer cell (e.g., a human breast cancer cell), (b) an optional linker component, and (c) one or more molecules having the ability to bind to an antigen presenting cell (e.g., a human macrophage). As described herein, BiPEs can be designed to include a molecule having the ability to bind to a cancer cell such as an anti-cancer antigen antibody (e.g., anti-human epidermal growth factor receptor 2 (HER2) antibody), a linker (e.g., a polypeptide-bases linker such as an amino acid segment or streptavidin and biotin components), and a molecule having the ability to bind to an APC such as a calreticulin (CRT). Such BiPEs can have the ability to facilitate the phagocytosis of cancer cells by APCs within a mammal's body and to activate down-stream adaptive immune responses (e.g., T cell responses) to treat cancer. In addition, the modular design of the BiPEs provided herein (e.g., a three component modular design) allows one to readily target tumors of different types or tumors of the same type but from different patients to personalize their therapy. The BiPEs provided herein also allow one to produce a universal cancer immunotherapy platform in a simple and economical manner.

In general, one aspect of this document features a composition comprising, or consisting essentially of, a first molecule having the ability to bind to cancer cells and a second molecule having the ability to bind to antigen presenting cells, wherein the first molecule is non-covalently linked to the second molecule, wherein incubation of the cancer cells and the antigen presenting cells in the presence of the composition results in increased phagocytosis of the cancer cells by the antigen presenting cells as compared to the level of phagocytosis of comparable cancer cells by comparable antigen presenting cells in the absence of the composition. The first molecule can comprise a streptavidin sequence, wherein the second molecule comprises a biotin sequence, and wherein the first molecule is non-covalently linked to the second molecule via a non-covalent linkage between the streptavidin sequence and the biotin sequence. The second molecule can comprise a streptavidin sequence, wherein the first molecule comprises a biotin sequence, and wherein the first molecule is non-covalently linked to the second molecule via a non-covalent linkage between the streptavidin sequence and the biotin sequence. The molecule having the ability to bind to cancer cells can be an anti-cancer antigen antibody. The anti-cancer antigen antibody can be an anti-CD340 antibody, an anti-EGFR antibody, or an anti-PSMA antibody. The molecule having the ability to bind to antigen presenting cells can be a polypeptide. The polypeptide can be a CRT polypeptide. The polypeptide can be a human CRT polypeptide. The cancer cells can be breast cancer cells, brain cancer cells, prostate cancer cells, lung cancer cells, or colorectal cancer cells. The cancer cells can be human breast cancer cells, human brain cancer cells, human prostate cancer cells, human lung cancer cells, or human colorectal cancer cells. The antigen presenting cells can be macrophages. The antigen presenting cells can be human macrophages. The increased phagocytosis can be at least a two-fold increase. The increased phagocytosis can be at least a four-fold increase.

In another aspect, this document features a fusion polypeptide comprising, or consisting essentially of, a first amino acid segment having the ability to bind to cancer cells and a second amino acid segment having the ability to bind to antigen presenting cells, wherein incubation of the cancer cells and the antigen presenting cells in the presence of the fusion polypeptide results in increased phagocytosis of the cancer cells by the antigen presenting cells as compared to the level of phagocytosis of comparable cancer cells by comparable antigen presenting cells in the absence of the fusion polypeptide. The first amino acid segment can be linked to the second amino acid segment via a linker amino acid sequence. The first amino acid segment having the ability to bind to cancer cells can be an anti-cancer antigen antibody. The anti-cancer antigen antibody can be an anti-CD340 antibody, an anti-EGFR antibody, or an anti-PSMA antibody. The second amino acid segment having the ability to bind to antigen presenting cells can be a CRT polypeptide. The CRT polypeptide can be a human CRT polypeptide. The cancer cells can be breast cancer cells, brain cancer cells, prostate cancer cells, lung cancer cells, or colorectal cancer cells. The cancer cells can be human breast cancer cells, human brain cancer cells, human prostate cancer cells, human lung cancer cells, or human colorectal cancer cells. The antigen presenting cells can be macrophages. The antigen presenting cells can be human macrophages. The increased phagocytosis can be at least a two-fold increase. The increased phagocytosis can be at least a four-fold increase.

In another aspect, this document features a method for treating a mammal having cancer. The method comprises, or consists essentially of, administering to the mammal a composition comprising, or consisting essentially of, a first molecule having the ability to bind to cancer cells and a second molecule having the ability to bind to antigen presenting cells, wherein the first molecule is non-covalently linked to the second molecule, wherein incubation of the cancer cells and the antigen presenting cells in the presence of the composition results in increased phagocytosis of the cancer cells by the antigen presenting cells as compared to the level of phagocytosis of comparable cancer cells by comparable antigen presenting cells in the absence of the composition. The first molecule can comprise a streptavidin sequence, wherein the second molecule comprises a biotin sequence, and wherein the first molecule is non-covalently linked to the second molecule via a non-covalent linkage between the streptavidin sequence and the biotin sequence. The second molecule can comprise a streptavidin sequence, wherein the first molecule comprises a biotin sequence, and wherein the first molecule is non-covalently linked to the second molecule via a non-covalent linkage between the streptavidin sequence and the biotin sequence. The molecule having the ability to bind to cancer cells can be an anti-cancer antigen antibody. The anti-cancer antigen antibody can be an anti-CD340 antibody, an anti-EGFR antibody, or an anti-PSMA antibody. The molecule having the ability to bind to antigen presenting cells can be a polypeptide. The polypeptide can be a CRT polypeptide. The polypeptide can be a human CRT polypeptide. The cancer cells can be breast cancer cells, brain cancer cells, prostate cancer cells, lung cancer cells, or colorectal cancer cells. The cancer cells can be human breast cancer cells, human brain cancer cells, human prostate cancer cells, human lung cancer cells, or human colorectal cancer cells. The antigen presenting cells can be macrophages. The antigen presenting cells can be human macrophages. The increased phagocytosis can be at least a two-fold increase. The increased phagocytosis can be at least a four-fold increase. The mammal can be a human. The cancer can be breast cancer, brain cancer, prostate cancer, lung cancer, or colorectal cancer. The composition can be administered by injection, ingestion, or inhalation.

In another aspect, this document features a method for treating a mammal having cancer. The method comprises, or consists essentially of, administering to the mammal a fusion polypeptide comprising, or consisting essentially of, a first amino acid segment having the ability to bind to cancer cells and a second amino acid segment having the ability to bind to antigen presenting cells, wherein incubation of the cancer cells and the antigen presenting cells in the presence of the fusion polypeptide results in increased phagocytosis of the cancer cells by the antigen presenting cells as compared to the level of phagocytosis of comparable cancer cells by comparable antigen presenting cells in the absence of the fusion polypeptide. The first amino acid segment can be linked to the second amino acid segment via a linker amino acid sequence. The first amino acid segment having the ability to bind to cancer cells can be an anti-cancer antigen antibody. The anti-cancer antigen antibody can be an anti-CD340 antibody, an anti-EGFR antibody, or an anti-PSMA antibody. The second amino acid segment having the ability to bind to antigen presenting cells can be a CRT polypeptide. The CRT polypeptide can be a human CRT polypeptide. The cancer cells can be breast cancer cells, brain cancer cells, prostate cancer cells, lung cancer cells, or colorectal cancer cells. The cancer cells can be human breast cancer cells, human brain cancer cells, human prostate cancer cells, human lung cancer cells, or human colorectal cancer cells. The antigen presenting cells can be macrophages. The antigen presenting cells can be human macrophages. The increased phagocytosis can be at least a two-fold increase. The increased phagocytosis can be at least a four-fold increase. The mammal can be a human. The cancer can be breast cancer, brain cancer, prostate cancer, lung cancer, or colorectal cancer. The composition can be administered by injection, ingestion, or inhalation.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 5. (a) Results of BiPE affinity assay in parent or EGFRvIII-expressing tumor cells treated for 2 hours with EGFRvIII-BiPE engineered with anti-EGFRvIII. EGFRvIII-BiPE was additionally labeled with a fluorescent marker (Alexa Fluor 647). Binding specificity was calculated as percent increase in fluorescent intensity (FI %) per well. (b) Affinity assay was repeated in the presence of EGFRvIII-blockade (pre, 10 mg/mL anti-EGFRvIII). * indicates statistically significant increase (p<0.05) (a-b). (c) EGFRvIII-BiPE phagocytosis assay in eFluor-670 labeled EGFRvIII-expressing cancer cells pre-treated for 2 hours with EGFRvIII-BiPE engineered with anti-EGFRvIII and CRT and co-cultured with CFSE-labeled bone marrow-derived phagocytes. Phagocytosis was calculated as dual eFluor-670/CFSE positive phagocytes over the total phagocyte population via flow cytometry. Phagocytic index was depicted as fold change increase where control (PBS) treated cells were set at 1.0. * indicated a minimum 0.5-fold change, which was considered significant (p<0.05).

DETAILED DESCRIPTION

This document provides methods and materials involved in treating cancer. For example, this document provides methods and materials for using BiPEs containing (a) one or more molecules having the ability to bind to a cancer cell (e.g., a human breast cancer cell) and (b) one or more molecules having the ability to bind to an APC (e.g., a human macrophage) to treat cancer.

The methods and materials provided herein can be used to treat any appropriate type of cancer. For example, the methods and materials provided herein can be used to treat breast cancer, brain cancer, prostate cancer, lung cancer, or colorectal cancer. In some cases, the methods and materials provided herein can be used to treat cancer (e.g., breast cancer) in any appropriate type of mammal including, without limitation, mice, rats, dogs, cats, horses, cows, pigs, monkeys, and humans.

In general, a BiPE provided herein can be designed to include a molecule having the ability to bind to a cancer cell and a molecule having the ability to bind to an APC. Examples of molecules having the ability to bind to a cancer cell that can be used to make a BiPE provided herein include, without limitation, antibodies such as anti-cancer antigen antibodies, non-antibody polypeptides, antibody fragments, and recombinant proteins. Examples of anti-cancer antigen antibodies having the ability to bind to a cancer cell that can be used to make a BiPE provided herein include, without limitation, anti-CD340 antibodies (e.g., anti-human epidermal growth factor receptor 2 (HER2) antibodies such as Herceptin), anti-EGFR antibodies (e.g., anti-human epidermal growth factor receptor antibodies), anti-EGFRviii antibodies (e.g., anti-human epidermal growth factor receptor variant 3 antibodies), anti-PSMA antibodies (e.g., anti-human prostate specific membrane antigen antibodies), anti-CEA antibodies (e.g., anti-human carcinoembryonic antigen antibodies), anti-CA125 antibodies (e.g., anti-human cancer antigen 125 antibodies), anti-CD20 antibodies (e.g., anti-human cluster antigen 20 antibodies), anti-CD30 antibodies, anti-CD33 antibodies, and anti-GD antibodies (anti-Gangliosides antibodies). In some cases, antibody fragments, nanobodies, full antibodies, or polypeptides can be used. Examples of non-antibody polypeptides having the ability to bind to a cancer cell that can be used to make a BiPE provided herein include, without limitation, RGD polypeptides, EGFR-specific polypeptides, and HER2 polypeptides.

Examples of molecules having the ability to bind to an APC that can be used to make a BiPE provided herein include, without limitation, antibodies, non-antibody polypeptides, and recombinant proteins. Examples of antibodies having the ability to bind to an APC that can be used to make a BiPE provided herein include, without limitation, anti-LRP1 antibodies, anti-SIRPalpha antibodies, and anti-complement receptor antibodies. In some cases, antibody fragments, nanobodies, or full antibodies can be used. Examples of non-antibody polypeptides having the ability to bind to an APC that can be used to make a BiPE provided herein include, without limitation, CRT polypeptides and complement polypeptides. Examples of non-antibody polypeptides having the ability to bind to an APC that can be used to make a BiPE provided herein include, without limitation, recombinant CRT, complement polypeptides, or bacterial polypeptides.

Figure 1:
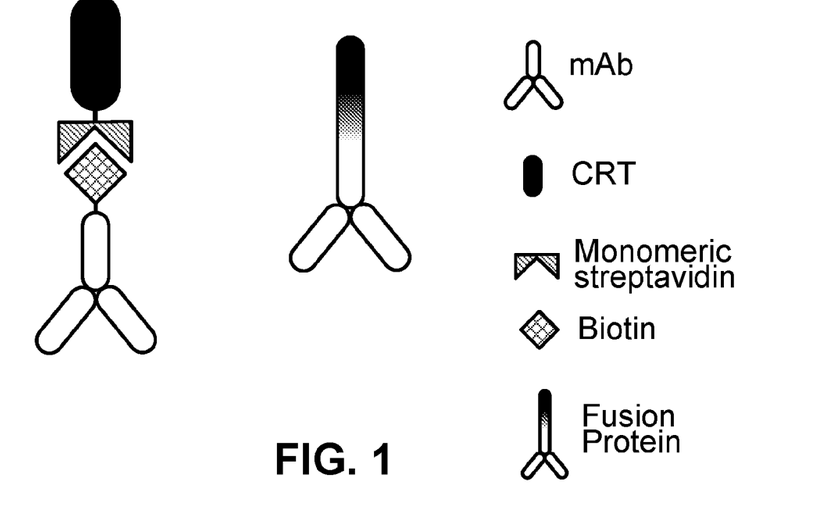
FIG. 1 is a schematic of two examples of BiPE modular configurations based on an all-protein design. The configuration on the left contains streptavidin and biotin linkers, and the configuration on the right uses an amino acid linker sequence within a fusion protein. The components can be interchangeable to create a "plug-and-play" library that targets a variety of tumor markers.

In some cases, a BiPE provided herein can be designed as shown in FIG. 1. For example, in some cases, a BiPE provided herein can be entirely composed of polypeptides or amino acids. In some cases, a BiPE provided herein can be a fusion protein composed of a single amino acid chain. In some cases, a BiPE provided herein can be a conjugate of different polypeptides that are non-covalently linked together. In some cases, streptavidin and biotin can be used to link the different polypeptide components together. Other examples of linkers that can be used to link (a) one or more molecules having the ability to bind to a cancer cell (e.g., a human breast cancer cell) and (b) one or more molecules having the ability to bind to an APC (e.g., a human macrophage) together include, without limitation, chemical linkers such as acylhydrazones and other polypeptide linkers (synthetic or biological).

In some cases, a BiPE provided herein can be designed to include a therapeutic agent, a label, and/or a contrast agent. For example, a BiPE provided herein can be designed to include one, two, three, four, five, six, or more therapeutic agents. Examples of therapeutic agents that can be incorporated into a BiPE provided herein include, without limitation, doxorubicin, cisplatin, carboplatin, temozolomide, docetaxel, and 5-FU. In some cases, a BiPE provided herein can be designed to include one, two, three, four, five, six, or more contrast agent materials. Examples of labels that can be incorporated into a BiPE provided herein include, without limitation, radioactive tracers or labels such as carbon-14 ($^{14}C$), hydrogen isotopes ($^{1}H$, $^{2}H$, $^{3}H$), and $^{13}N$, polypeptide tags such as green fluorescent protein (GFP), and epitope tags such as FLAG, poly-His, and glutathione-S-transferase (GST). Examples of contrast agent materials that can be incorporated into a BiPE provided herein include, without limitation, gadolinium, iodide, iron oxide, FDG, radioisotopes, and organic dyes.

In some cases, a BiPE provided herein can have the ability to facilitate the phagocytosis of cancer cells by APCs within a mammal's body and to activate down-stream adaptive immune responses (e.g., T cell responses) to treat cancer. For example, a BiPE provided herein can be designed to recognize simultaneously cancer cells (which can deliver the BiPE to the area of interest, can limit non-specific immune reactions, and can spare normal surrounding tissues, thereby minimizing adverse effects) and APCs (which can enable these cells to initiate the first stages of a cancer cell clearance process). The ability to home and heighten the localization of APC's to the tumor microenvironment can increase tumor phagocytosis (e.g., tumor cell internalization). Once internalized, APCs can present fragments of the tumor antigens to the membrane surface via MHC molecules on the cell surface. This, in turn, can enhance T cell recognition of the cancer cells within a mammal.

As described herein, a BiPE provided herein can be administered to a mammal to treat cancer. Any appropriate method can be used to administer a BiPE provided herein to a mammal. For example, a BiPE provided herein can be administered via injection (e.g., subcutaneous injection, intramuscular injection, intravenous injection, or intrathecal injection).

Before administering a BiPE provided herein to a mammal, the mammal can be assessed to determine whether or not the mammal has cancer (e.g., breast cancer). Any appropriate method can be used to determine whether or not a mammal has cancer. For example, a mammal (e.g., human) can be identified as having cancer using standard diagnostic techniques. In some cases, a tissue biopsy can be collected and analyzed to determine whether or not a mammal has cancer.

After identifying a mammal as having cancer (e.g., breast cancer), the mammal can be administered a composition containing one or more BiPEs provided herein. For example, a composition containing a BiPE provided herein can be administered prior to or in lieu of surgical resection of a tumor. In some cases, a composition containing a BiPE provided herein can be administered following resection of a tumor.

A composition containing a BiPE provided herein can be administered to a mammal in any appropriate amount, at any appropriate frequency, and for any appropriate duration effective to achieve a desired outcome (e.g., to increase progression-free survival). In some cases, a composition containing a BiPE provided herein can be administered to a mammal having cancer (e.g., breast cancer) to reduce the progression rate of the cancer by 5, 10, 25, 50, 75, 100, or more percent. For example, the progression rate can be reduced such that no additional cancer progression is detected. Any appropriate method can be used to determine whether or not the progression rate of cancer is reduced. For example, the progression rate of cancer can be assessed by imaging tissue at different time points and determining the amount of cancer cells present. The amounts of cancer cells determined within tissue at different times can be compared to determine the progression rate. After treatment as described herein, the progression rate can be determined again over another time interval. In some cases, the stage of cancer after treatment can be determined and compared to the stage before treatment to determine whether or not the progression rate was reduced.

In some cases, a composition containing a BiPE provided herein can be administered to a mammal having cancer (e.g., breast cancer) under conditions where progression-free survival is increased (e.g., by 5, 10, 25, 50, 75, 100, or more percent) as compared to the median progression-free survival of corresponding mammals having untreated cancer (e.g., untreated breast cancer). Progression-free survival can be measured over any appropriate length of time (e.g., one month, two months, three months, four months, five months, six months, or longer).

An effective amount of a composition containing a BiPE provided herein can be any amount that reduces the progression rate of cancer (e.g., breast cancer), increases the progression-free survival rate, or increases the median time to progression without producing significant toxicity to the mammal. Typically, an effective amount of a composition containing a BiPE provided herein can be from about 100 mg/m$^2$ to about 200 mg/m$^2$. If a particular mammal fails to respond to a particular amount, then the amount of a composition containing a BiPE provided herein can be increased by, for example, two fold. After receiving this higher concentration, the mammal can be monitored for both responsiveness to the treatment and toxicity symptoms, and adjustments made accordingly. The effective amount can remain constant or can be adjusted as a sliding scale or variable dose depending on the mammal's response to treatment. Various factors can influence the actual effective amount used for a particular application. For example, the frequency of administration, duration of treatment, use of multiple treatment agents, route of administration, and severity of the cancer (e.g., breast cancer) may require an increase or decrease in the actual effective amount administered.

The frequency of administration can be any frequency that reduces the progression rate of cancer (e.g., skin cancer), increases the progression-free survival rate, or increases the median time to progression without producing significant toxicity to the mammal. For example, the frequency of administration can be from about once a month to about three times a month, or from about twice a month to about six times a month, or from about once every two months to about three times every two months. The frequency of administration can remain constant or can be variable during the duration of treatment. A course of treatment with a composition containing a BiPE provided herein can include rest periods. For example, a composition containing a BiPE provided herein can be administered over a two week period followed by a two week rest period, and such a regimen can be repeated multiple times. As with the effective amount, various factors can influence the actual frequency of administration used for a particular application. For example, the effective amount, duration of treatment, use of multiple treatment agents, route of administration, and severity of the cancer may require an increase or decrease in administration frequency.

An effective duration for administering a composition containing a BiPE provided herein can be any duration that reduces the progression rate of cancer (e.g., breast cancer), increases the progression-free survival rate, or increases the median time to progression without producing significant toxicity to the mammal. Thus, the effective duration can vary from several days to several weeks, months, or years. In general, the effective duration for the treatment of cancer can range in duration from several weeks to several months. In some cases, an effective duration can be for as long as an individual mammal is alive. Multiple factors can influence the actual effective duration used for a particular treatment. For example, an effective duration can vary with the frequency of administration, effective amount, use of multiple treatment agents, route of administration, and severity of the cancer (e.g., breast cancer).

A composition containing a BiPE provided herein can be in any appropriate form. For example, a composition containing a BiPE provided herein can be in the form of a solution or powder with or without a diluent to make an injectable suspension. A composition containing a BiPE provided herein also can contain additional ingredients including, without limitation, pharmaceutically acceptable vehicles. A pharmaceutically acceptable vehicle can be, for example, saline, water, lactic acid, mannitol, or combinations thereof.

After administering a composition containing a BiPE provided herein to a mammal, the mammal can be monitored to determine whether or not the cancer (e.g., breast cancer) was treated. For example, a mammal can be assessed after treatment to determine whether or not the progression rate of cancer was reduced (e.g., stopped). As described herein, any method can be used to assess progression and survival rates.

The invention will be further described in the following examples, which do not limit the scope of the invention described in the claims.

EXAMPLES

Figure 2:
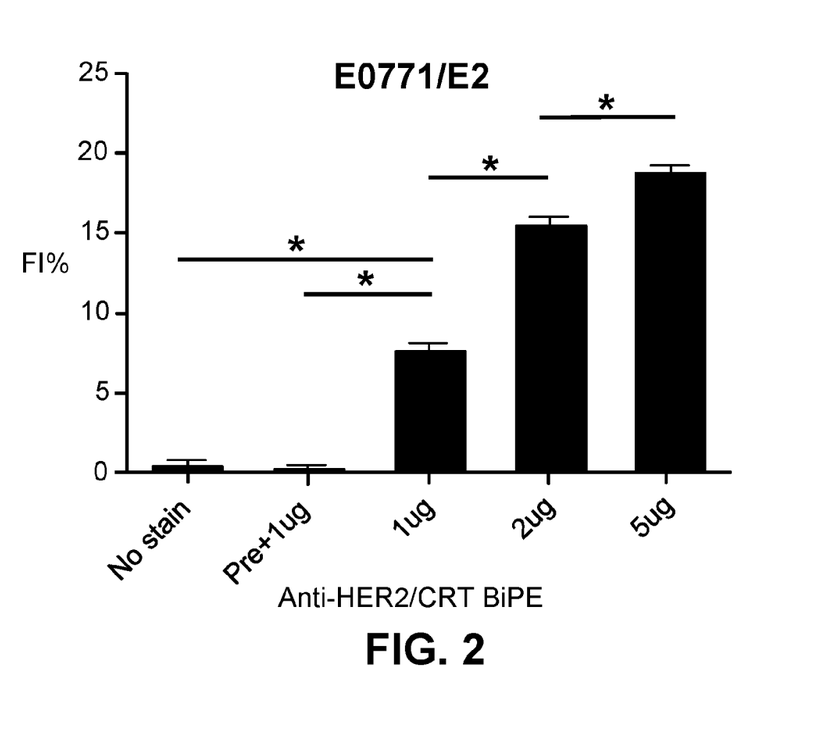
FIG. 2 contains results of an HER2-BiPE affinity assay in HER2-expressing tumor cells (E0771/E2) treated for 2 hours with HER2-BiPE engineered with Trastuzumab. HER2-BiPE was additionally labeled with a fluorescent marker (Alexa Fluor 647). Binding specificity was calculated by % increase in fluorescent intensity (FI %) per well. HER2-blockade (Pre) was achieved by pretreating cells with 21 mg/mL of Trastuzumab. * indicates statistically significant increase ($p<0.05$).

Example 1—a Modular Designed Bi-Specific Phagocyte Engager (BiPE) for Cancer Immunotherapy Expression of the receptor tyrosine kinase erbB-2, commonly referred to as HER2 and encoded by the gene ERBB2, of the HER/EGFR/ERBB receptor family, is amplified in about 30 percent of breast cancer (Mitri et al., *Chemotherapy Research and Practice*, Vol. 2012:Article ID 743193 (2012)). Trastuzumab (Herceptin®), a monoclonal antibody that binds specifically to HER2, was ligated to a recombinant CRT protein using a monomeric streptavidin/biotin complex, thereby forming a BiPE designated HER2-BiPE. The HER2-BiPE was labeled with a fluorescent marker (Alexa Fluor 647). Dose-dependent HER2-specific binding of HER2-BiPE to HER2-expressing E0771/E2 tumor cells was confirmed (FIG. 2). In addition, the binding was completely abrogated when the cells were pretreated with Trastuzumab, which blocked available HER2 binding sites (FIG. 2).

Figure 3A:
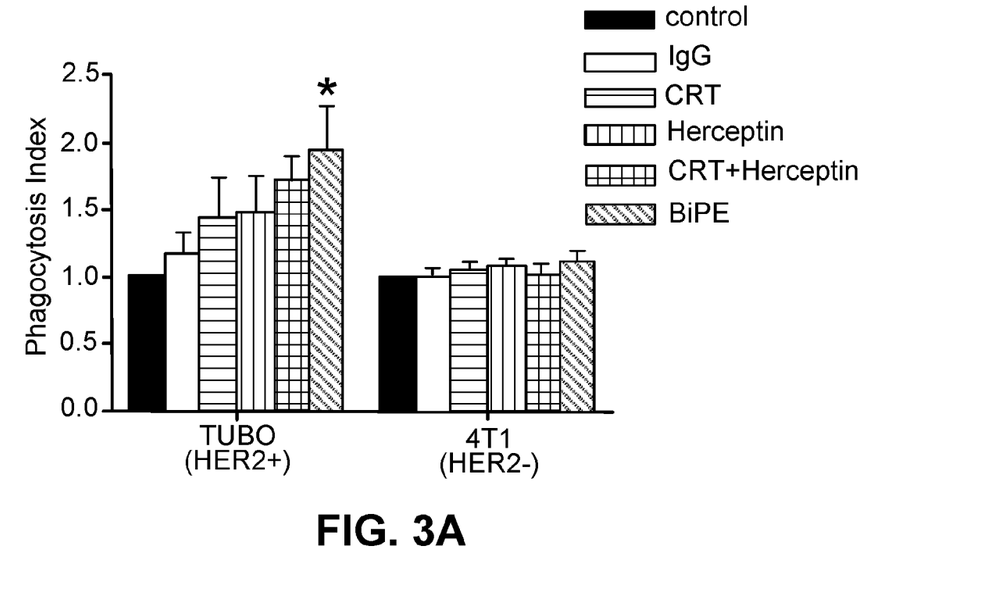
FIGS. 3A and 3B contain results of an HER2-BiPE phagocytosis assay in eFluor-670 labeled breast cancer cells pre-treated for 2 hours with HER2-BiPE engineered with Trastuzumab/CRT and co-cultured with CFSE-labeled bone marrow-derived phagocytes. Phagocytosis was calculated as dual eFluor-670/CFSE positive phagocytes over the total phagocyte population via flow cytometry. Phagocytic index was depicted as fold change increase, where control (PBS) treated cells were set at 1.0. * indicates a minimum 0.5-fold change, which was considered significant ($p<0.05$).
Figure 3B:
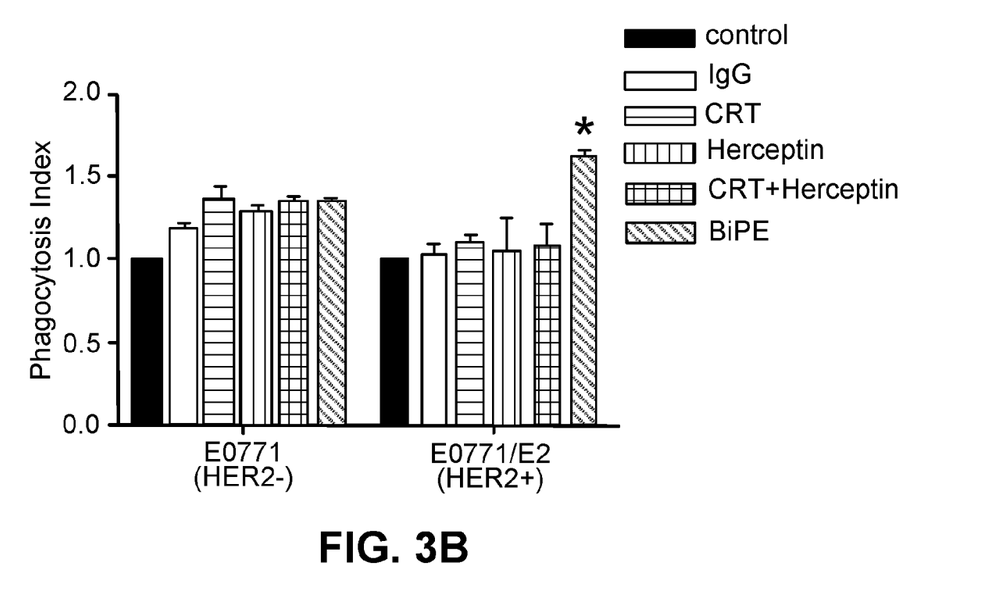

The activation of antigen presenting cells in response to HER2-BiPE was examined using a phagocytosis assay with a variety of patient-derived and syngeneic murine models of breast cancer that either express HER2 (TUBO, E0771/E2) or are HER2-deficient (4T1, E0771) (FIGS. 3A and 3B). HER2-BiPE activated phagocytes in a HER2-dependent manner, as maximal phagocytosis was observed with HER2-expressing tumor cells treated with the fully assembled BiPE construct as compared to control and as compared to treatment with non-ligated components (CRT alone, Trastuzumab alone, or CRT plus Trastuzumab as an unligated mixture) (FIGS. 3A and 3B).

Figure 4:
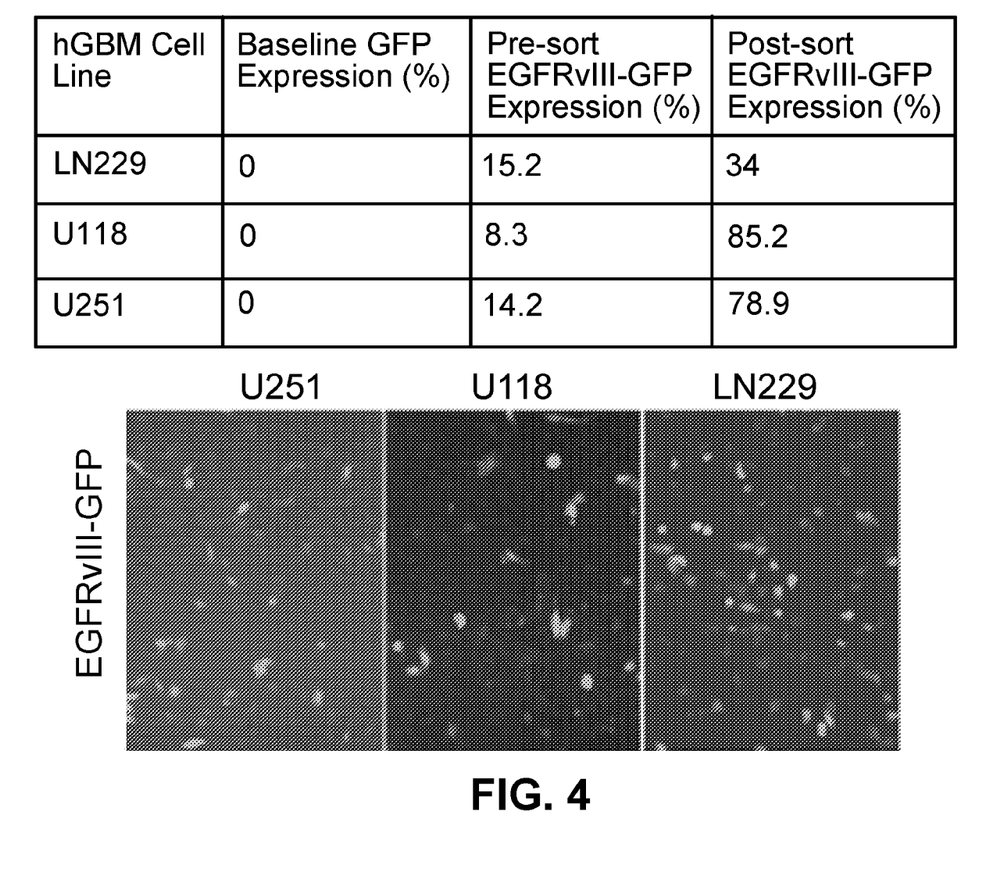
FIG. 4. Patient-derived glioblastoma cells with no baseline EGFRvIII expression were engineered to over-express GFP-labeled EGFRvIII. Cells were sorted by flow cytometry to enrich EGFRvIII-overexpressing population as detected by GFP.
Figure 5A:
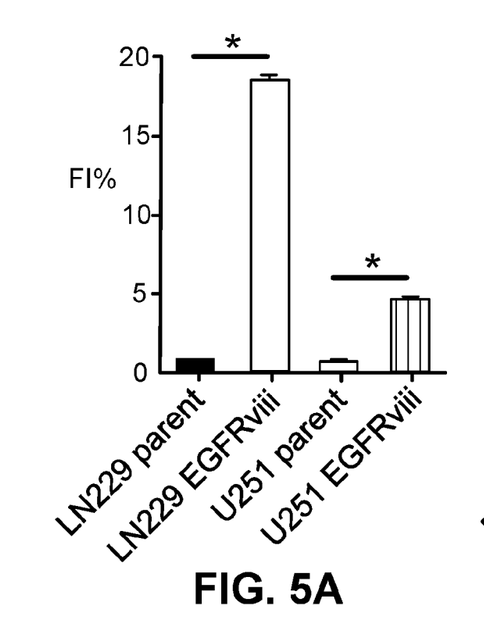
Figure 5B:
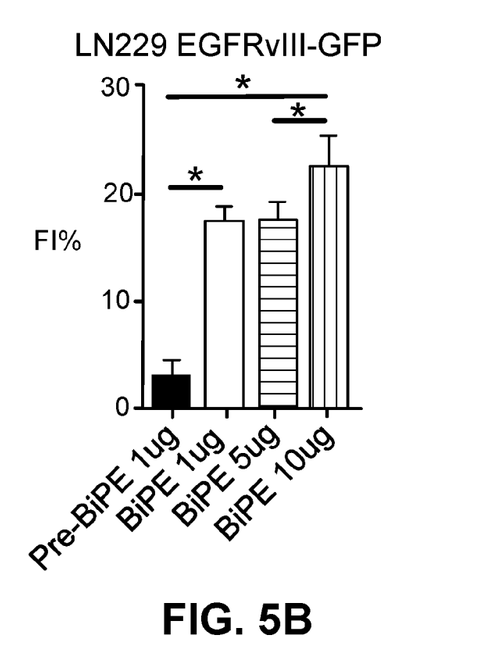
Figure 5C:
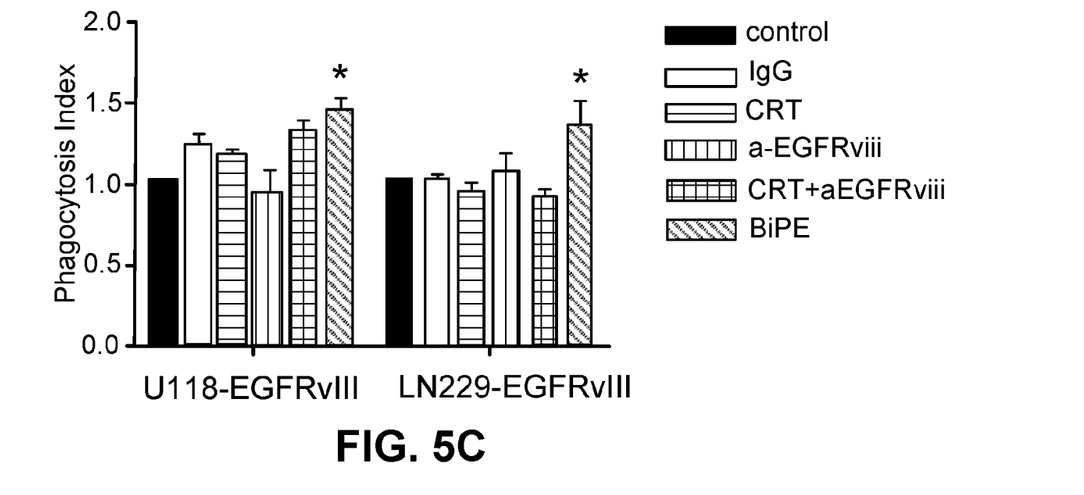

The effectiveness of BiPEs against aggressive brain cancer (glioblastoma; GBM) also was tested. Overexpression of the epidermal growth factor receptor (EGFR) is a commonly associated genetic variation in GBM tumors (frequency of about 34-63 percent), with EGFR variant III (EGFRvIII; a tumor-specific variant of EGFR) presenting in a large proportion of cases (frequency of about 25-64%) (Gan et al., *FEBS J.*, 280 (21):5350-70 (2013)). To create a GBM-specific BiPE, a commercially available EGFRvIII monoclonal antibody was ligated to CRT using a monomeric streptavidin/biotin complex, thereby forming a BiPE designated EGFRvIII-BiPE. The targeting ability and immunomodulatory behavior of the EGFRvIII-BiPE was tested in human GBM cell models. To generate appropriate cell models, a GFP-labeled EGFRvIII expression construct was transfected into several patient-derived GBM cell lines (FIG. 4). Binding specificity of EGFRvIII-BiPE was determined by affinity assay, demonstrating binding of EGFRvIII-BiPE only in cells expressing EGFRvIII (FIG. 5A), which was blocked with pretreatment of cells with anti-EGFRvIII (FIG. 5B). Activation of antigen presenting cells in response to EGFRvIII-BiPE was evaluated using a phagocytosis assay. EGFRvIII-BiPE activated phagocytes in an EGFRvIII-dependent manner, as maximal phagocytosis was observed with EGFRvIII-expressing tumor cells treated with the fully assembled EGFRvIII-BiPE construct as compared to control and as compared to treatment with non-ligated components (CRT alone, anti-EGFRvIII alone, and CRT plus anti-EGFRvIII as an unligated mixture) (FIG. 5C).

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A composition comprising a first molecule having an ability to bind to cancer cells and a second molecule having an ability to bind to antigen presenting cells, wherein said first molecule is non-covalently linked to said second molecule, wherein incubation of said cancer cells and said antigen presenting cells in said presence of said composition results in increased phagocytosis of said cancer cells by said antigen presenting cells as compared to said level of phagocytosis of comparable cancer cells by comparable antigen presenting cells in said absence of said composition, wherein said first molecule comprises an anti-CD340 antibody, an anti-epidermal growth factor receptor (EGFR) antibody, an anti-epidermal growth factor receptor variant 3 (EGFRviii) antibody, an anti-prostate specific membrane antigen (PSMA) antibody, an anti-carcinoembryonic antigen (CEA) antibody, an anti-cancer antigen 125 (CA125) antibody, an anti-CD20 antibody, an anti-CD30 antibody, an anti-CD33 antibody, or an anti-ganglioside antibody, and wherein said second molecule comprises an anti-low density lipoprotein receptor-related protein 1 (LRP1) antibody, anti-signal regulatory protein α (SIRPα) antibody, an anti-complement receptor antibody, or a calreticulin (CRT) polypeptide.

2. The composition of claim 1, wherein said first molecule comprises a streptavidin sequence, wherein said second molecule comprises a biotin sequence, and wherein said first molecule is non-covalently linked to said second molecule via a non-covalent linkage between said streptavidin sequence and said biotin sequence.

3. The composition of claim 1, wherein said second molecule comprises a streptavidin sequence, wherein said first molecule comprises a biotin sequence, and wherein said first molecule is non-covalently linked to said second molecule via a non-covalent linkage between said streptavidin sequence and said biotin sequence.

4. The composition of claim 1, wherein said first molecule comprises said anti-EGFR antibody.

5. The composition of claim 1, wherein said first molecule comprises said anti-CD340 antibody, said anti-EGFR antibody, or said anti-PSMA antibody.

6. The composition of claim 1, wherein said second molecule comprises said calreticulin (CRT) polypeptide.

7. The composition of claim 6, wherein said calreticulin (CRT) polypeptide is a human calreticulin (CRT) polypeptide.

8. The composition of claim 1, wherein said first molecule comprises said anti-EGFR antibody and said second molecule comprises said calreticulin (CRT) polypeptide.

9. The composition of claim 1, wherein said increased phagocytosis is at least a four-fold increase.

* * * * *